(12) United States Patent
Pauws et al.

(10) Patent No.: US 10,431,343 B2
(45) Date of Patent: Oct. 1, 2019

(54) SYSTEM AND METHOD FOR INTERPRETING PATIENT RISK SCORE USING THE RISK SCORES AND MEDICAL EVENTS FROM EXISTING AND MATCHING PATIENTS

(71) Applicant: KONINKLIJKE PHILIPS N.V., Eindhoven (NL)

(72) Inventors: Steffen Clarence Pauws, Eindhoven (NL); Jorn Op Den Buijs, Eindhoven (NL); Daniele De Massari, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 193 days.

(21) Appl. No.: 15/607,967

(22) Filed: May 30, 2017

(65) Prior Publication Data

US 2017/0337345 A1 Nov. 23, 2017

(30) Foreign Application Priority Data

May 23, 2016 (EP) .................................... 16172132

(51) Int. Cl.
| | |
|---|---|
| G06F 19/00 | (2018.01) |
| G06F 19/24 | (2011.01) |
| G01N 5/02 | (2006.01) |
| G16H 50/70 | (2018.01) |
| G06Q 50/24 | (2012.01) |
| G06N 5/02 | (2006.01) |
| G16B 40/00 | (2019.01) |
| G16H 50/20 | (2018.01) |

(52) U.S. Cl.
CPC ........... *G16H 50/70* (2018.01); *G06F 19/321* (2013.01); *G06N 5/022* (2013.01); *G06Q 50/24* (2013.01); *G16B 40/00* (2019.02); *G16H 50/20* (2018.01)

(58) Field of Classification Search
CPC ....... G06F 19/24; G06F 19/321; G06N 5/022; G06Q 50/24; G16H 50/20; G16H 50/70
USPC ........ 702/179, 180, 181, 183, 187; 600/301, 600/509, 515; 705/2, 3, 36 R
See application file for complete search history.

(56) References Cited

U.S. PATENT DOCUMENTS

| | | |
|---|---|---|
| 2003/0191666 A1 | 10/2003 | Kline |
| 2008/0162182 A1 | 7/2008 | Cazares et al. |
| 2010/0016743 A1 | 1/2010 | Syed et al. |

(Continued)

FOREIGN PATENT DOCUMENTS

| | | |
|---|---|---|
| EP | 1640888 A2 | 3/2006 |
| WO | 2009083833 A1 | 7/2009 |
| WO | 2014052921 A2 | 4/2014 |

*Primary Examiner* — John H Le (57) ABSTRACT

There is provided a computer-implemented method and apparatus for determining a likelihood of occurrence of a medical event for a subject. A risk profile for the subject is acquired and a plurality of risk profiles for other subjects are obtained from a database. The acquired subject risk profile is compared to the obtained plurality of other subject risk profiles. At least one risk profile is selected from the obtained plurality of other subject risk profiles that most closely matches the acquired subject risk profile. The likelihood of occurrence of a medical event for the subject is determined based on the selected at least one risk profile. A signal indicative of the determined likelihood of occurrence of the medical event for the subject is output.

15 Claims, 5 Drawing Sheets

(56) References Cited

U.S. PATENT DOCUMENTS

| | | |
|---|---|---|
| 2014/0095184 A1 | 4/2014 | Gotz et al. |
| 2014/0257122 A1 | 9/2014 | Ong et al. |
| 2015/0324530 A1 | 11/2015 | Heywood et al. |
| 2016/0135706 A1* | 5/2016 | Sullivan ............... A61B 5/0059 |
| | | 600/301 |
| 2016/0374608 A1* | 12/2016 | Dugan ................ A61B 5/6831 |
| | | 600/301 |

* cited by examiner

SYSTEM AND METHOD FOR INTERPRETING PATIENT RISK SCORE USING THE RISK SCORES AND MEDICAL EVENTS FROM EXISTING AND MATCHING PATIENTS

CROSS-REFERENCE TO PRIOR APPLICATIONS

This application claims the benefit of European Patent Application No. 16172132.9, filed on 2016 May 31. This application is hereby incorporated by reference herein.

TECHNICAL FIELD OF THE INVENTION

The invention relates to the field of determining a likelihood of occurrence of a medical event for a subject (for example, a patient) and, in particular, determining the likelihood of occurrence of the medical event using a risk profile for the subject.

BACKGROUND TO THE INVENTION

The computerized estimation and predictive analysis of healthcare related data for subjects is becoming increasingly more valuable since it means that appropriate healthcare can be provided to subjects more efficiently and effectively. This form of predictive analytics can be used to build prognostic models from data (for example, using statistical or machine learning methods) to estimate the probability (i.e. likelihood or risk) of the occurrence of a medical event and/or to estimate any future benefit or success to be achieved by circumventing the occurrence of that medical event. There are many techniques based around prognostic models for public and clinical health including preventive intervention, diagnostics, treatment planning, outcome prediction, clinical deterioration detection, and so on.

In the domain of clinical deterioration detection, a prognostic model estimates a short-term risk of an upcoming worsening episode of a chronically ill patient who is remotely managed by telehealth. A timely and reliable estimate allows for an early intervention before a hospitalization is warranted. Such a prognostic model is constructed from the vital sign measurements (such as body weight, heart rate, blood pressure and SpO2 for heart failure patient) and self-reported signs and symptoms (such as fatigue, shortness of breath and oedema for a heart failure patient) with an unplanned hospitalization event as a predicted outcome. These prognostic models are based on a simple analysis of data to determine any change in the condition of a subject such as whether the condition of the subject has worsened, improved or remained stable. At discharge of a subject admitted for an acute event, prognostic models can be used in deciding on the best discharge treatment options (such as the use of telehealth or community services). Prognostic models can also be useful in patient monitoring. For example, prognostic models can assist in clinical decision making and alert clinical staff on patient deterioration, and can be useful for the patient, his peers and healthcare professionals in deciding on a care plan to be followed, an immediate intervention, decision making, lifestyle changes or treatment and/or patient education.

In some existing models, a risk score can be determined for a subject over time and the risk score can be used to provide an insight into the health of a subject over time. However, the correct interpretation of a subject risk score is subtle as there are different meanings of "risks", and such interpretation may be critical for adequately assessing a subject health condition(s), thereby determining the appropriate course of action for this subject. There is a risk defined at population or cohort level (sometimes called an epidemiological risk or group risk), which entails estimating a mean risk from a group of subjects. There is also a risk coupled to a single individual (sometimes called the clinical risk or individual risk), which reflects an outcome estimation for a target subject with a known set of values for the variables in a prognostic model.

Additionally, in some existing models, risk scores are essentially used as probabilities and thus only make sense for a group of subjects. For example, if a risk score expresses that the chance of hospitalization is 20% for a group of 100 subjects, this means that 20 subjects in that group on average will experience a hospitalization. This makes it difficult to relate an outcome of a risk score analysis to a particular individual subject as an individual risk is only equal to a group risk if all members of the group are equally likely to experience a hospitalization. In addition, risk scores are only estimates and thus are not always accurate. This means that risk scores can be unreliable and may result in false alarms.

At the same time, current techniques for analyzing risk scores are slow. For example, the lack of a link between a group estimated risk score and an individual subject often means that further analysis of data acquired from the subject is required by healthcare professionals before a decision can be taken on the healthcare to provide to the subject. However, any delay in analyzing risk scores can prove critical since time is often short and limited in the healthcare field. Thus, in the existing models that use risk scores, serious events can be missed.

Therefore, there is a need for a method (e.g. a computer implemented method) and apparatus that can determine a likelihood of occurrence of a medical event for a subject in a more robust, reliable and efficient manner.

SUMMARY OF THE INVENTION

As noted above, a limitation with risk analysis is that it can be unreliable and inefficient, and may therefore, when carried by a suitable computer means (such as processing unit), lead to important i) delay in processing time, and/or ii) loss of processing capabilities that would be at better use for another task. In order to overcome the above problems, it would be valuable to have a more reliable and efficient method for determining a likelihood of occurrence of a medical event for a subject (for example, a patient) through risk analysis.

Therefore, according to a first aspect of the invention, there is provided a method, preferably a computer-implemented method for determining a likelihood of occurrence of a medical event for a subject, the method comprising: acquiring a risk profile for the subject; obtaining a plurality of risk profiles for other subjects from a database; comparing the acquired subject risk profile to the obtained plurality of other subject risk profiles; selecting at least one risk profile from the obtained plurality of other subject risk profiles that most closely matches the acquired subject risk profile of the subject; determining the likelihood of occurrence of a medical event for the subject based on the selected at least one risk profile; and outputting a signal indicative of the determined likelihood of occurrence of the medical event for the subject. It is thus possible to more reliably and efficiently determine a likelihood of occurrence of a medical event for a subject (for example, a patient) through risk analysis. The subjects are compared on a single unitary scale and data that is relevant and useful to individual subjects is provided in a time-efficient way. The data that is compared is simplified in the form of a risk profile, which enables the data to be processed more efficiently. This conserves processing resources and power. Also, a user is provided with a notification or information on any possible medical event such that an appropriate action or intervention can be taken. Moreover, a more reliable clinical picture of the subject is provided by the computer-implemented method such that an improved diagnosis and more effective treatment is possible.

In some embodiments, the subject risk profile may comprise a time series of risk scores for the subject. In some embodiments, the other subject risk profiles may comprise a time series of risk scores for the other subjects. The time series of risk scores for the subject can prove useful in the comparison of risk profiles. Moreover, it possible to perceive the progress of the risk scores over time (for example, whether the risk scores increase over time, decrease over time or remain constant over time). As the subject risk profile comprises a time series of risk scores for the subject, the likelihood of occurrence of the medical event for the subject can be determined for a certain time period. In this way, it can be decided whether and at which point in time an intervention may be necessary. This information can be useful in prioritising subjects for interventions, enabling a more efficient use of time for medical professionals. Furthermore, the dynamic nature of taking into account a time series of risk scores means that it is possible to identify false positives. The dynamic nature of taking into account a time series of risk scores also means that critical medical events are less likely to be missed. A more reliable clinical picture of the subject is thus provided in this way, which enables improved diagnosis and more effective treatment.

In some embodiments, the method may comprise time-aligning the time series of risk scores in the obtained plurality of other subject risk profiles with the risk scores in the acquired subject risk profile and comparing the acquired subject risk profile to the obtained plurality of other subject risk profiles may comprise comparing the time-aligned risk profiles. In this way, a more reliable determination of a likelihood of occurrence of a medical event for a subject can be provided, thereby enabling improved diagnosis and more effective treatment.

In some embodiments, a risk profile from the obtained plurality of other subject risk profiles that most closely matches the acquired subject risk profile may be a risk profile that has the same or similar risk scores over time to the risk scores for the subject. In this way, the risk profile selected will more accurately reflect the subject and thus a determination of the likelihood of occurrence of a medical event for the subject made based on the selected risk profile is more reliable, minimizing false positives and avoiding potentially critical medical events being missed.

In some embodiments, similar risk scores may be risk scores that differ by less than a predefined value from the risk scores for the subject. In this way, it is possible to extract the risk profiles that will provide the most accurate and reliable determination of a health condition for the subject.

In some embodiments, the medical event for the subject may be a deterioration in one or more physiological characteristics and/or vital signs of the subject. In this way, it is possible to determine a deterioration of the health condition of the subject such that a user (for example, the subject themselves, a caregiver, a family member, a peer, or a healthcare professional) can decide on whether action needs to be taken to prevent occurrence of a medical event.

In some embodiments, the subject risk profile may comprise a plurality of risk scores for the subject and the obtained plurality of other subject risk profiles may comprise respective risk scores for the other subjects.

In some embodiments, selecting at least one risk profile from the obtained plurality of other subject risk profiles that most closely matches the acquired subject risk profile may comprise selecting at least one risk profile from the obtained plurality of other subject risk profiles comprising risk scores that most closely match the respective risk scores of the subject risk profile. In this way, the gap between a group estimated risk score and an individual subject is bridged. The risk profile selected from the other subject risk profiles will provide the most accurate and reliable reflection of the health of the subject.

In some embodiments, the subject risk profile may comprise a plurality of risk scores for the subject and the obtained plurality of other subject risk profiles may comprise respective risk scores for the other subjects, and selecting at least one risk profile from the obtained plurality of other subject risk profiles that most closely matches the acquired subject risk profile may comprise selecting at least one risk profile from the obtained plurality of other subject risk profiles comprising risk scores that are within a pre-defined range of the respective risk scores of the subject risk profile. In this way, it is possible to extract the risk profiles that will provide the most accurate and reliable determination of a health condition for the subject.

In some embodiments, comparing the acquired subject risk profile to the obtained plurality of other subject risk profiles may comprise dividing the acquired subject risk profile and the obtained plurality of other subject risk profiles into a plurality of segments and comparing the segments of the acquired subject risk profile with corresponding segments of the obtained plurality of other subject risk profiles. In this way, a more refined analysis of the risk scores is possible, wherein selecting at least one risk profile from the obtained plurality of other subject risk profiles that most closely matches the acquired subject risk profile may comprise selecting at least one risk profile from the obtained plurality of other subject risk profiles that has a segment comprising risk scores that most closely match the risk scored of the corresponding segment of the acquired subject risk profile. In this way, an improved determination of reliable risk profiles to use for a particular subject in determining the likelihood of occurrence of a medical event for that subject is achieved. The more refined analysis of risk scores through a segment comparison and the selection based on this segment comparison ensures that the risk profile that most accurately reflects the health of a particular subject is chosen, thereby providing a more reliable determination of the likelihood of occurrence of a medical event for that subject.

In some embodiments, the method may comprise forecasting the time series of risk scores for the subject in a predetermined time frame based on a time series of risk scores in the selected at least one risk profile and determining the likelihood of occurrence of a medical event for the subject based on the selected at least one risk profile may comprise determining the likelihood of occurrence of a medical event for the subject based on the forecasted time series of risk scores for the subject. In this way, the risk scores can be analyzed for varying lengths of time (e.g. over a certain number of hours, days, months, and so on). By the use of time frames in this way, the chances of catching a medical event in sufficient time for an appropriate action to be taken is improved and intelligence on the amount of time available to prevent or change the occurrence of the medical event is provided. This improves the reliability of a healthcare system that employs the method.

In some embodiments, determining the likelihood of occurrence of a medical event for the subject based on the selected at least one risk profile may comprise identifying whether a medical event occurred for the subject of the selected at least one risk profile and/or identifying whether a medical intervention occurred for the subjects of the selected at least one risk profile, and determining the likelihood of occurrence of a medical event for the subject based on the identification. This improves the reliability of catching medical events before they occur in that medical events are less likely to be missed.

In some embodiments, determining the likelihood of occurrence of a medical event for the subject based on the identification may comprise determining the likelihood of occurrence of a medical event for the subject as the percentage of the selected at least one risk profile for which a medical event occurred for the subject of the selected at least one risk profile or for which a medical intervention occurred.

In some embodiments, the method may further comprise determining whether a medical intervention is to be implemented for the subject based on the determined likelihood of occurrence of the medical event and outputting a signal indicative of the determination. In this way, a user is provided with an indication as to whether a medical intervention is necessary and appropriate action can be taken more quickly.

In some embodiments, the subject risk profile may be based on one or more physiological characteristics of the subject, one or more symptoms of the subject, clinical information for the subject and/or demographical information for the subject.

According to a second aspect of the invention, there is provided a computer program product comprising a computer readable medium, the computer readable medium having computer readable code embodied therein, the computer readable code being configured such that, on execution by a suitable computer or processor, the computer or processor is caused to perform the method or the methods described above.

According to a third aspect of the invention, there is provided an apparatus for determining a likelihood of occurrence of a medical event for a subject, the apparatus comprising a control unit configured to: acquire a risk profile for the subject; obtain a plurality of risk profiles for other subjects from a database; compare the acquired subject risk profile to the obtained plurality of other subject risk profiles; select at least one risk profile from the obtained plurality of other subject risk profiles that most closely matches the acquired subject risk profile; determine the likelihood of occurrence of a medical event for the subject based on the selected at least one risk profile; and wherein the apparatus further comprises an output unit operatively connected to the control unit configured to output a signal indicative of the determined likelihood of occurrence of the medical event for the subject. It is thus possible to more reliably and efficiently determine a likelihood of occurrence of a medical event for a subject (for example, a patient) through risk analysis. The subjects are compared on a single unitary scale and data that is relevant and useful to individual subjects is provided in a time-efficient way. The data that is compared is simplified in the form of a risk profile, which enables the data to be processed more efficiently. This conserves processing resources and power. Also, a user is provided with a notification or information on any possible medical event such that an appropriate action or intervention can be taken. Moreover, a more reliable clinical picture of the subject is provided by the apparatus such that an improved diagnosis and more effective treatment is possible.

In some embodiments, the subject risk profile may be based on one or more physiological characteristics of the subject, one or more symptoms of the subject, clinical information for the subject, and/or demographic information for the subject, and the control unit may be configured to acquire the one or more physiological characteristics of the subject by controlling a physiological characteristic sensor to measure the one or more physiological characteristics of the subject, and to acquire the one or more symptoms of the subject, the clinical information of the subject, and/or demographic information for the subject from a user interface device. In this way, the control unit can easily and effectively acquire data that can be processed to reliably and efficiently determine a likelihood of occurrence of a medical event for a subject.

In some embodiments, the apparatus may be part of a general purpose computing device.

By interpreting a risk profile for the subject through a comparison with risk profiles for other subjects (such as those having a similar risk profile to the subject), it is possible to decide whether to implement an action (such as an intervention) or take no action. Examples of actions that may be implemented include, but are not limited to, administering a medication to the subject, changing a medication administered to the subject, calling the subject, changing the posture or pose of the subject, or any other action or combination thereof. The action may be implemented by the subject, a caregiver, a family member, a peer, or a healthcare professional.

It is thus possible to more reliably and efficiently determine a likelihood of occurrence of a medical event for a subject.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

As noted above, the invention provides a method and apparatus that can determine a likelihood of occurrence of a medical event for a subject (for example, a patient) in a more reliable and efficient manner, which overcomes the existing problems with risk analysis.

Figure 1:
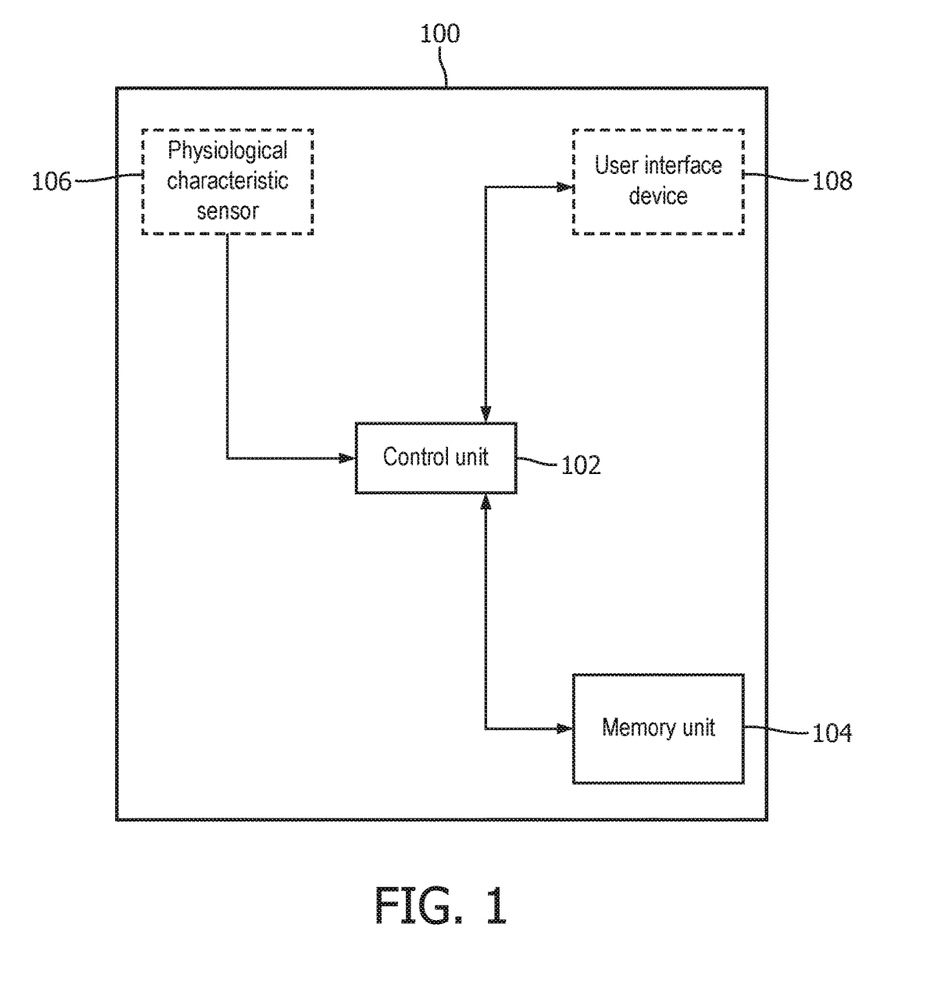
FIG. 1 is a block diagram of an apparatus according to an embodiment of the invention.

FIG. 1 shows a block diagram of an apparatus 100 according to an embodiment of the invention that can be used for determining a likelihood of occurrence of a medical event for a subject (for example, a patient). The subject may, for example, be a patient such as a patient that requires monitoring for healthcare reasons. A medical event may be any event (for example, any incident or situation) where the health of the subject is adversely affected (for example, adversely impacted or influenced). Examples of a medical event include, but are not limited to, an increase in the severity, acuity and/or stage of a disease in the subject, an onset or worsening of a medical condition for the subject, a detrimental impact on the well-being of the subject, a deterioration of a health condition of the subject (for example, a deterioration in one or more physiological characteristics or vital signs of the subject), a death of the subject, or any other event where the health of the subject is adversely affected, or any combination thereof. In some embodiments, a medical event may be any event that necessitates or requires intervention from a medical practitioner or another person.

The apparatus 100 comprises a control unit 102 that controls the operation of the apparatus 100 and that can implement the method describe herein. Briefly, the control unit 102 is configured to acquire a risk profile for a subject (i.e. a subject risk profile). A risk profile may comprise a time series of risk scores for the subject. In some embodiments, the risk profile is based on one or more physiological characteristics of a subject (such as heart rate, blood pressure, skin conductivity, brain activity, breathing rate, muscle activity, or any other physiological characteristics or combination of physiological characteristics), one or more symptoms of a subject (such as shortness of breath, fatigue, headache, pain, vomiting, insomnia, swelling of ankles, or any other symptoms or combination of symptoms), clinical information for the subject (such as the medical condition of the subject, any medication that the subject is on, a left ventricular ejection fraction (LVEF) for the subject, levels of N-terminal pro-brain natriuretic peptide (NT-proBNP) in the subject, whether the subject suffers from hypertension, or any other clinical information, or any combination of clinical information), and/or demographic information for the subject (such as gender, age, body weight, body mass index BMI, occupation, race, level of education, area of living, or any other demographic information or combination of demographic information).

In some embodiments, the risk scores in the risk profile may be values. For example, the risk scores in the risk profile may be values determined based on one or more physiological characteristics of a subject, one or more symptoms of a subject and/or demographic information for the subject such as any of those mentioned above or any combination thereof. A value for a risk score is indicative of a risk of a medical event occurring. As mentioned earlier, a medical event may be any event (for example, any incident or situation) where the health of the subject is adversely affected (for example, adversely impacted or influenced). Thus, a value for a risk score can be indicative of a risk of an event occurring where the health of the subject is adversely affected. The value for a risk score can, for example, be an integer value on a scale (such as an integer value on a scale of 1 to 10, on a scale of 1 to 100, or on any other scale) or a percentage value (such as a percentage value between 0% and 100%). The higher the value of a risk score, the more the subject is at risk of a medical event occurring.

The apparatus 100 comprises a memory unit 104 that can be used for storing program code that can be executed by the control unit 102 to perform the method described herein. The memory unit 104 can also be used to store information, data, signals and measurements made or acquired by any sensors or devices that are part of the apparatus 100 or that are external to the apparatus 100.

In some embodiments, the control unit 102 of the apparatus 100 can be configured to acquire the subject risk profile from the memory unit 104 in the apparatus 100.

Alternatively, the control unit 102 of the apparatus 100 can be configured to acquire the subject risk profile from memory unit external to the apparatus 100. In some embodiments, the control unit 102 of the apparatus 100 can itself be configured to acquire the subject risk profile by determining the risk profile for the subject based on data or information that the control unit 102 acquires from one or more memory units, one or more devices and/or sensors, or any combination thereof. The one or more memory units may include the memory unit 104 in the apparatus 100 and/or one or more external memory units. Similarly, the one or more devices and sensors may be part of the apparatus 100 or may be external to the apparatus 100.

For example, in some embodiments, the control unit 102 can be configured to acquire one or more physiological characteristics of the subject, one or more symptoms of the subject, clinical information for the subject and/or demographic information for the subject from the memory unit 104 in the apparatus 100 or from a memory unit external to the apparatus 100 and use the acquired one or more physiological characteristics of the subject, one or more symptoms of the subject, clinical information for the subject and/or demographic information for the subject in determining the subject risk profile. In some embodiments, the symptoms of the subject, clinical information for the subject and/or demographic information for the subject may be acquired through self-reports or surveys. A self-report or survey may include questions directed to the health and wellbeing of the subject (for example, "how do you feel today?", "do you have swollen ankles today?", and so on). The questions posed in a self-report or survey may be tailored or personalized to a subject. For example, certain questions may be posed to subjects of a particular group (e.g. subjects of the same age group, subjects from the same location, and so on).

In some embodiments, the apparatus 100 may comprise a physiological characteristic sensor 106 configured to acquire one or more physiological characteristics of the subject that can be used in determining the subject risk profile. The control unit 102 of the apparatus 100 can be configured to acquire the one or more physiological characteristics of the subject by controlling the physiological characteristic sensor 106 in the apparatus 100 to measure one or more physiological characteristics of the subject.

In other embodiments, the control unit 102 of the apparatus 100 may be configured to acquire the one or more physiological characteristics of the subject from an external physiological characteristic sensor (i.e. a physiological characteristic sensor that is separate from the apparatus 100). In other words, the apparatus 100 comprising the control unit 102 and the memory unit 104 may be remote from the physiological characteristic sensor. In this embodiment, the apparatus 100 and physiological characteristic sensor may be part of a remote telehealth-enabled system. Here, the control unit 102 of the apparatus 100 may be configured to determine, manage and process the risk profiles of multiple subjects. The physiological characteristic sensor can be part of a device configured for home use and the apparatus 100 can be located at a remote healthcare facility (e.g. a hospital, a general practice, a medical call center or similar). The physiological characteristic sensor can be configured to acquire physiological characteristics of the subject and transmit the acquired physiological characteristics to the control unit 102 of the apparatus 100 via a network. The control unit 102 of the apparatus 100 is thus configured to acquire physiological characteristics by receiving the physiological characteristics via the network from one or more physiological characteristic sensors. The control unit 102 can determine risk scores for subjects from the physiological characteristics received for those subjects and the risk scores may be displayed on a user interface device for clinical interpretation.

In some embodiments, multiple physiological characteristics can be acquired by one or multiple physiological characteristic sensors. The output of a physiological characteristic sensor may be a time series of values for the physiological characteristic, or 'raw' measurements (for example, measurements of heart rate, an ECG signal, and so on) that are processed by the control unit 102 in order to determine a time series of values for the physiological characteristic.

In some embodiments, the physiological characteristic sensor 106 may be a blood pressure sensor for acquiring blood pressure measurements of the subject. The blood pressure sensor can be any type of device that is able to measure the blood pressure of a subject. For example, the blood pressure sensor can be in the form of a cuff-based device. In this example, a cuff is placed around a limb (for example, an arm) or digit (for example, a finger) of the subject, a pump is used to inflate the cuff to a desired pressure, and a pressure sensor measures the air pressure inside the cuff The pump may also be configured to deflate the cuff to a desired pressure and/or the device can comprise a valve that can be controlled to deflate the cuff. A processor or control unit in the device (or alternatively the control unit 102) can analyze the measurements from the air pressure sensor and control the pump and/or valve to inflate and/or deflate the cuff accordingly to obtain a measurement of the blood pressure of the subject. In an example, the blood pressure of the subject can be acquired by measuring sound distal from the cuff (known as the auscultatory method) or by measuring pressure pulsations in the cuff caused by volume pulsations of the arm and brachial artery and extracting features from the envelope of these pressure pulses (known as the oscillometric method). Those skilled in the art will be aware of cuff-based devices and other types of devices (e.g. that do not use a cuff) that can be used to measure blood pressure.

In some embodiments, the physiological characteristic sensor 106 may be a skin conductivity sensor for acquiring skin conductivity measurements (i.e. galvanic skin response). Skin conductance can be measured using a pair of electrodes that are placed in contact with the skin of the subject. An electrical current may be applied through one of the electrodes and the resistance of the skin measured, or the voltage between the electrodes can be measured. In an exemplary embodiment, the electrodes can be configured to be in contact with the skin on the palm of a hand of the subject.

In some embodiments, the physiological characteristic sensor 106 may be a heart rate sensor for acquiring heart rate measurements of the subject. The heart rate sensor may be any type of heart rate sensor. In one example, the heart rate sensor may be an electrocardiogram (ECG) sensor and the heart rate measurement of the subject may be acquired from an ECG signal (i.e. a signal representing the electrical activity of the subject's heart) measured by the ECG sensor. The ECG sensor may comprise at least two electrodes. In the example of an ECG sensor comprising two electrodes, the electrodes may be located either side of the subject's heart (for example, located on each arm). However, those skilled in the art will be aware of other arrangements for the electrodes on the body of the subject to acquire a heart rate measurement of the subject. In another example, the heart rate sensor may be a photo-plethysmography (PPG) sensor and the heart rate measurement of the subject may be acquired from a PPG signal measured by the PPG sensor. In other examples, the heart rate sensor can be an accelerometer located on the chest or back of the subject (with an acceleration measurement signal being processed to identify accelerations/movements due to the beating of the heart), a microphone located on the chest or back of the subject (with the sound measurement signal being processed to identify sounds that occur due to the beating of the heart) or a blood oxygenation (SpO2) sensor.

Other examples of physiological characteristic sensors 106 can include a brain activity sensor for acquiring brain activity measurements (such as electrodes for acquiring electroencephalography, EEG, measurements) of the subject, a breathing (i.e. respiration) rate sensor for acquiring breathing rate measurements of the subject, a muscle activity sensor for acquiring muscle activity measurements of the subject (such as an electromyograph for acquiring electromyography, EMG, measurements), a skin temperature sensor for acquiring skin temperature measurements of the subject, a blood glucose sensor for acquiring blood glucose levels for the subject, and an oxygen saturation monitoring device for acquiring oxygen saturation readings for the subject.

Although some examples have been provided for the physiological characteristic sensor 106 and the physiological characteristic, those skilled in the art will be aware of other physiological characteristic sensors 106 that can be used and other types of physiological characteristics that can be acquired. In some embodiments, a combination of physiological characteristic sensors 106 can be used to acquire more than one type of physiological characteristic.

In some embodiments, the apparatus 100 may comprise a user interface device 108 for acquiring one or more symptoms of the subject, clinical information for the subject, and/or demographic information for the subject, which can be used in determining the subject risk profile. As mentioned earlier, the symptoms of the subject may include shortness of breath, fatigue, headache, pain, vomiting, insomnia, swelling of ankles, or any other symptoms, or any combination of symptoms. The clinical information for the subject may include the medical condition of the subject, any medication that the subject is on, a left ventricular ejection fraction (LVEF) for the subject, levels of N-terminal pro-brain natriuretic peptide (NT-proBNP) in the subject, whether the subject suffers from hypertension, or any other clinical information, or any combination of clinical information. The demographic information for the subject may include gender, age, BMI, occupation, race, level of education, area of living, or any other demographic information or combination of demographic information.

The control unit 102 of the apparatus 100 can be configured to acquire one or more symptoms of the subject, clinical information for the subject and/or demographic information for the subject from the user interface device 108 in the apparatus 100.

In other embodiments, the control unit 102 of the apparatus 100 may be configured to acquire the one or more symptoms of the subject, clinical information for the subject and/or demographic information for the subject from an external user interface device (i.e. a user interface device that is separate from the apparatus 100). In other words, the apparatus 100 comprising the control unit 102 and the memory unit 104 may be remote from the user interface device. In this embodiment, the apparatus 100 and user interface device may be part of a remote telehealth-enabled system, as described earlier. The user interface device can be part of a device configured for home use and the apparatus 100 can be located at a remote healthcare facility (e.g. a hospital, a general practice, a medical call center or similar). The user interface device can be configured to acquire information from the subject and transmit the acquired information to the control unit 102 of the apparatus 100 via a network. The control unit 102 of the apparatus 100 is thus configured to acquire symptoms of the subject, clinical information for the subject and/or demographic information for the subject by receiving the information via the network from one or more user interface devices. The control unit 102 can determine risk scores for subjects from the information received for those subjects and the risk scores may be displayed on a user interface component for clinical interpretation. The user interface component and the physiological sensor may be part of the same device configured for home use.

In some embodiments, multiple types of symptoms, clinical information and/or demographic information can be acquired by one or multiple user interface devices. In one embodiment, the output of a user interface device may be a time series of values associated with the symptoms (for example, that indicate the severity of those symptoms), or 'raw' data (for example, the symptoms themselves) that is processed by the control unit 102 in order to determine a time series of values for the symptoms.

A user interface device 108 may be or may comprise means that enables the subject or another user of the apparatus 100 to interact with and/or control the apparatus 100. In some embodiments, the user interface device 108 can be any device capable of receiving a user input such as a touch screen, a keyboard, a keypad, or any of device capable of receiving a user input. The user interface device 108 may comprise a switch, a button or other control means for activating and deactivating the apparatus 100 and/or process of acquiring or obtaining risk profiles.

Although some examples have been provided for the user interface device 108, the symptoms, the clinical information and the demographic information, those skilled in the art will be aware of other user interface devices 108 that can be used and other types of symptoms, clinical information and demographic information. In some embodiments, a combination of user interface devices 108 can be used to acquire more than one type of symptom, clinical information and/or demographic information. In some embodiments, the clinical information and/or demographic information may be acquired from the memory unit 104 in the apparatus 100 or from a memory unit external to the apparatus 100.

Where the control unit 102 of the apparatus 100 acquires one or more physiological characteristics, one or more symptoms of the subject, clinical information for the subject and/or demographic information for the subject, the control unit 102 is configured to acquire a risk profile for the subject (i.e. the subject risk profile) by determining the subject risk profile based on the acquired one or more physiological characteristics, one or more symptoms of the subject, clinical information for the subject and/or demographic information for the subject.

In some embodiments, the control unit 102 may be configured to acquire the subject risk profile in any of the manners described above from any combination of a memory unit 104 in the apparatus 100, an external memory unit, a sensor in the apparatus 100 (such as the physiological characteristic sensor 106), an external sensor, a device in the apparatus 100 (such as the user interface device 108), and an external device such as any of those described above.

The control unit 102 is also configured to obtain a plurality of risk profiles for other subjects (i.e. a plurality of other subject risk profiles). As with the risk profile acquired for the subject, the other subject risk profiles may comprise a time series of risk scores for the other subjects and can be based on one or more physiological characteristics of the other subjects, one or more symptoms of the other subjects, clinical information for the other subjects and/or demographic information for the other subjects. The control unit 102 is configured to obtain the plurality of other subject risk profiles from a database (such as a database of previously acquired risk profiles). In some embodiments, the memory unit 104 of the apparatus 100 can comprise the database from which the plurality of other subject risk profiles are obtained. Alternatively, a memory unit external to the apparatus 100 may comprise the database from which the plurality of other subject risk profiles are obtained.

The database of risk profiles for subjects may be updated to include new profiles or to modify existing profiles at predetermined time intervals. For example, the database of risk profiles may be updated on a regular basis (such as an hourly or daily basis), at irregular time intervals (such as times in which data is obtained from the subject using a personal healthcare system at home), or at periodic time intervals (such as at times where the subject data is obtained from the subject during a visit to a professional healthcare facility).

The acquired subject risk profile and the obtained plurality of other subject risk profiles can be processed generally as they are acquired or obtained (for example, in real-time or near-real time), or they can be stored in the memory unit 104 of the apparatus 100 and the control unit 102 of the apparatus 100 can retrieve and process the previously acquired subject risk profile and the obtained plurality of other subject risk profiles from the memory unit 104 at a later time.

The control unit 102 can comprise one or more processors, processing units, multi-core processors or modules that are configured or programmed to control the apparatus 100 to determine the likelihood of occurrence of a medical event for the subject based on the selected at least one risk profile. In particular implementations, the control unit 102 can comprise a plurality of software and/or hardware modules that are each configured to perform, or are for performing, individual or multiple steps of the method according to embodiments of the invention.

In some embodiments, the control unit 102 (and thus the apparatus 100) may be part of a device (for example, a computer or a mobile device such as a smart phone, a tablet, a portable computer, or similar) or any other general purpose computing device that can comprise, be connected to or otherwise acquire or obtain risk profiles for subjects. In other embodiments, the apparatus 100 can be an apparatus that is dedicated to the purpose of acquiring or obtaining risk profiles for subjects.

It will be appreciated that FIG. 1 only shows the components required to illustrate this aspect of the invention, and in a practical implementation the apparatus 100 may comprise additional components to those shown. For example, the apparatus 100 may comprise a battery or other power supply for powering the apparatus 100 or means for connecting the apparatus 100 to a mains power supply, and/or a communication module for enabling acquired or obtained risk profiles for subjects to be communicated to a base unit for the apparatus 100 or to a remote computer (for example, that is operated by a healthcare professional).

The apparatus 100 may also comprise an output unit (not shown) operatively connected to the control unit 102 for use in providing the subject or other user of the apparatus 100 (for example, healthcare provider) with information resulting from the method according to the invention. The output unit can comprise any component that is suitable for providing the information resulting from the method according to the invention, and can be, for example, any one or more of a display screen or other visual indicator, a speaker, one or more lights, and a component for providing tactile feedback (e.g. a vibration function). The control unit 102 is configured to output a signal indicative of the determined likelihood of occurrence of the medical event for the subject, which may be output via the output unit. Specifically, the output unit can be configured to output the signal indicative of the determined likelihood of occurrence of the medical event for the subject.

Figure 2:
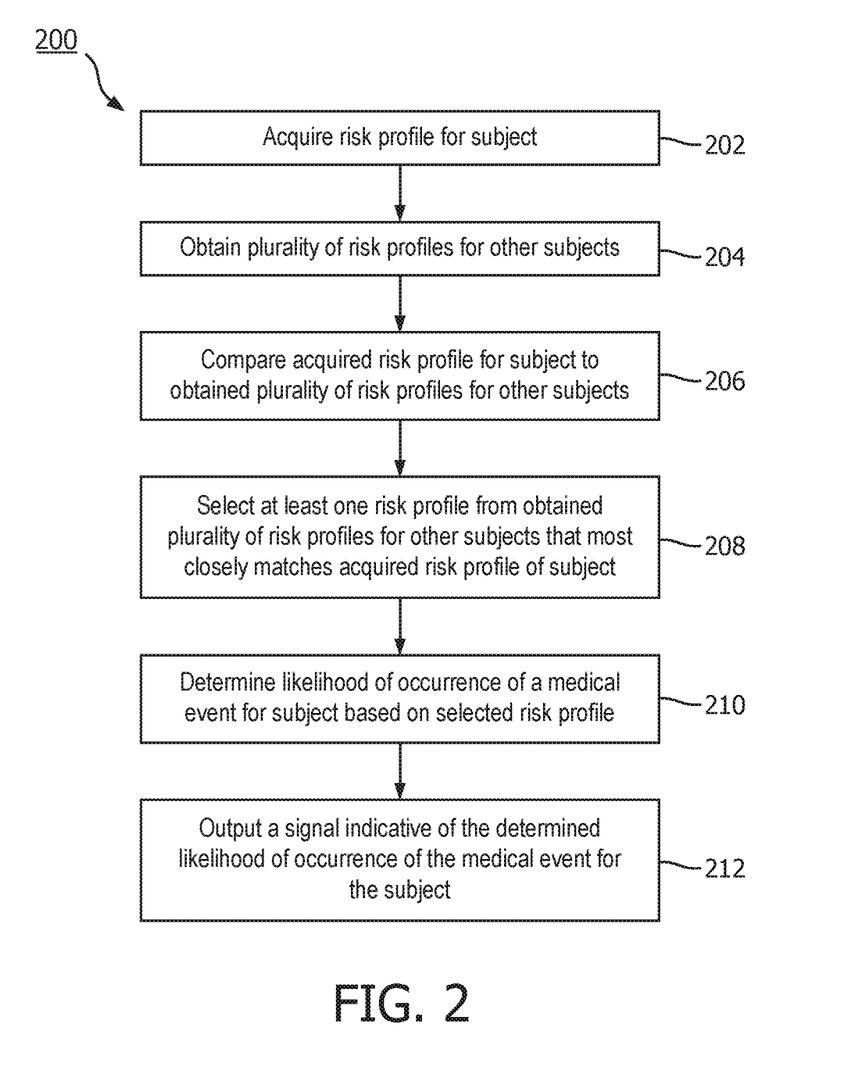
FIG. 2 is a flow chart illustrating a method according to an embodiment of the invention.

FIG. 2 illustrates a method 200 for determining a likelihood of occurrence of a medical event for a subject according to an embodiment of the invention. This method can generally be performed by or under the control of the control unit 102 of the apparatus 100.

With reference to FIG. 2, at block 202, a risk profile for a subject is acquired (i.e. a subject risk profile is acquired). As described above, the acquired subject risk profile may comprise a time series of risk scores for the subject. The acquired subject risk profile can be based on one or more physiological characteristics of the subject, one or more symptoms of the subject, clinical information for the subject and/or demographic information for the subject. The subject risk profile can be acquired directly (for example, using a sensor such as a physiological characteristic sensor and/or a device such as a user interface device) or can be retrieved from a memory unit. As described earlier, the sensor, device and memory unit can either be part of the apparatus 100 or separate to the apparatus 100.

At block 204, a plurality of risk profiles are obtained for other subjects (i.e. a plurality of other subject risk profiles are obtained) from a database. As described above, the obtained plurality of other subject risk profiles may also comprise a time series of risk scores for the other subjects. The obtained plurality of other subject risk profiles can be based on one or more physiological characteristics of the other subjects, one or more symptoms of the other subjects, clinical information for the other subjects and/or demographic information for the other subjects. The database from which the other subject risk profiles are obtained can be a database in the memory unit 104 of the apparatus 100 or a database in a memory unit external to the apparatus 100.

At block 206, the acquired subject risk profile is compared to the obtained plurality of other subject risk profiles. In other words, the acquired subject risk profile (or the time series of risk scores in the subject risk profile) are matched to the risk scores of the obtained plurality of other subject risk profiles.

In one embodiment, a time series of risk scores in the obtained plurality of other subject risk profiles is time-aligned with the risk scores in the acquired subject risk profile. This time-alignment may be based on the comparison at block 206, as described above. This time alignment may be performed for every subject that has a risk profile in the database or a subset of subjects that have a risk profile in the database. The acquired subject risk profile is then compared to the time-aligned obtained plurality of other subject risk profiles. For example, a risk score in the acquired subject risk profile is compared to a corresponding risk scores in the obtained plurality of other subject risk profiles (i.e. risk scores that are determined to be at the same positions in time are compared).

In some embodiments, the acquired subject risk profile and the obtained plurality of other subject risk profiles are divided into a plurality of segments and the segments of the acquired subject risk profile are compared with corresponding segments of the obtained plurality of other subject risk profiles. The number or size of the segments is customizable by a user of the apparatus 100. In some embodiments, the segments may be used to compare subjects having a common characteristic such as subjects from the same age group, suffering from the same disease, with a similar medical history, having an event occur in the same time period, having been hospitalized, or any other common characteristic.

At block 208, at least one risk profile is selected from the obtained plurality of other subject risk profiles that most closely matches (i.e. differs the least from or is the most similar or close to) the acquired subject risk profile. In some embodiments, only the risk profiles of other subjects having a characteristic in common with the subject are obtained (for example, only the other subjects having the same or a similar health condition as the subject, in the same age group, or the like).

The subject risk profile may comprise a plurality of risk scores for the subject and the obtained plurality of other subject risk profiles may comprise respective risk scores for the other subjects. In some embodiments, at least one risk profile is selected from the obtained plurality of other subject risk profiles that comprises risk scores that most closely match respective risk scores of the subject risk profile (i.e. the nearest neighbor profile is selected). In this embodiment, the comparison of the time-aligned acquired subject risk profile and obtained plurality of other subject risk profiles may be analyzed to determine at least one of the obtained plurality of other subject risk profiles that has a sub-series of risk scores that is amongst the closest matches with a selected series of risk scores from the acquired subject risk profile.

In other embodiments, at least one risk profile is selected from the obtained plurality of other subject risk profiles that comprises risk scores that are within a predefined range of the respective risk scores in the subject risk profile (i.e. range matching is performed). In this embodiment, the comparison of the time-aligned acquired subject risk profile and obtained plurality of other subject risk profiles may be analyzed to determine at least one of the obtained plurality of other subject risk profiles that has a sub-series of risk scores that can be found within a predefined range of a selected series of risk scores from the acquired subject risk profile. The size of the predefined range is customizable by a user of the apparatus 100.

In other embodiments where segments of the acquired subject risk profile are compared with corresponding segments of the obtained plurality of other subject risk profiles, at least one risk profile is selected from the obtained plurality of other subject risk profiles as the risk profile that has a segment most closely matching the corresponding segment of the acquired subject risk profile (i.e. interval matching is performed). For example, at least one risk profile may be selected from the obtained plurality of other subject risk profiles that has a segment comprising risk scores that most closely match the risk scores of the corresponding segment of the acquired subject risk profile. In this embodiment, the comparison of the time-aligned acquired subject risk profile and obtained plurality of other subject risk profiles may be divided into a set of intervals (i.e. segments) to determine at least one of the obtained plurality of other subject risk profiles that has a sub-series of risk scores that can be found to share the same interval as a selected series of risk scores from the acquired subject risk profile. As mentioned earlier, the number or size of the segments is customizable by a user of the apparatus 100.

In some embodiments, the total number of risk profiles selected may be confined to a maximum value. For example, a risk profile may be selected from the obtained plurality of other subject risk profiles if the time-aligned risk profile is amongst M closest matches, where M is a maximum value for the total number of risk profiles that can be selected. The maximum value M may be any integer value such as 5, 10, 15 or 20. However, these are only example values and those skilled in the art will understand that the maximum value M can be any other integer value. The maximum value M is customizable by a user of the apparatus 100.

In some embodiments, a risk profile from the obtained plurality of other subject risk profiles that most closely matches the acquired subject risk profile is a risk profile that has the same risk scores or similar risk scores (for example, risk scores that differ the least) over time to the risk scores for the subject. In other words, a risk profile from the obtained plurality of other subject risk profiles that most closely matches the acquired subject risk profile may be a risk profile that has the most similar trend in risk scores over time to the risk scores for the subject. Similar risk scores are risk scores that differ by less than a predefined value from the risk scores for the subject. The predefined value for determining whether a risk score is similar to a corresponding risk score for the subject may be expressed as a percentage. For example, a risk score may be considered similar to a subject risk score if that risk score differs from the subject risk score by less than a predefined percentage (such as less than 30%, less than 25%, less than 20%, less than 15%, less than 10%, less than 5% or any intervening value).

In some embodiments where the subject risk profile is based on one or more physiological characteristics of the subject, one or more symptoms of the subject, clinical information for the subject and/or demographic information for the subject, the selected at least one risk profile can be a risk profile that is based on the same or similar physiological characteristics, symptoms, clinical information and/or demographic information as the subject risk profile.

For example, the selected at least one risk profile can be a risk profile that is determined to have the same or a similar rise in blood pressure as the subject risk profile (such as a blood pressure rise that has the same gradient, or a gradient that differs by less than a predefined value). In another example, the selected at least one risk profile can be a risk profile for a subject that has the same or similar symptoms as another subject. In this example, similar symptoms may include at least one symptom in common or at least one corresponding symptom. In another example, the selected at least one risk profile can be a risk profile for a subject that has the same or a similar medical condition as another subject. In this example, a similar medical condition may be a medical condition that falls under the same category of medical conditions. For example, medical conditions that fall under a respiratory condition category may be considered similar even where the condition itself is not identical (for example, asthma and bronchitis may be considered similar medical conditions since both of these conditions affect respiration). In another example, the selected at least one risk profile can be a risk profile for a subject that is the same or a similar age as another subject. In this example, a similar age may be an age that falls within a predetermined range of the age of the subject (such as a range of 1 year, 2 years, 3 years, 4 years, 5 years, or any other integer number of years from the age of the subject). For example, where the subject is 24 years old, a similar age may be an age between 20 and 30 years old, and so on.

Where the obtained plurality of other subject risk profiles comprise risk scores at irregular intervals or have risk scores missing, the comparison technique can be adjusted to account for this. For example, the risk scores may be placed on a regular time grid to account for the irregular intervals and missing risk scores can be input by a user of the apparatus 100 or computed by the control unit 102 of the apparatus 100 using dynamic programming or a learning technique.

Although examples have been provided for comparing (or matching) the obtained plurality of other subject risk profiles to the acquired subject risk profile, those skilled in the art will understand that any other comparison (or matching) technique can be used.

At block 210, the likelihood (or probability) of occurrence of a medical event for the subject is determined based on the selected at least one risk profile. In some embodiments, the medical event for the subject is a deterioration of the health condition of the subject. For example, the medical event for the subject may be a deterioration in one or more physiological characteristics and/or vital signs of the subject.

In some embodiments, the time series of risk scores for the subject in a predetermined time frame is forecasted (i.e. extrapolated or predicted) based on a time series of risk scores in the selected at least one risk profile. In this way, any change in risk score in the predetermined time frame can be observed. The predetermined time frame can be any time frame such as a predetermined number of hours, days, weeks, months, or similar. The forecast provides a user of the apparatus 100 with details of how the risk score may change if no action is taken (for example, no intervention). The likelihood of occurrence of a medical event for the subject is then determined based on the forecasted time series of risk scores for the subject, i.e. it is determined whether a medical event is likely to occur in the predetermined time frame.

In one exemplary embodiment, this information can be used to determine the likely effect (or impact) on the risk score of the subject if the subject were to undergo a treatment by observing the risk scores of the other subjects with similar risk profiles that have undergone the treatment and the risk scores of the other subjects with similar risk profiles that have not undergone the treatment.

The forecasting of a time series of risk scores can be realized through autoregressive modelling of the time series of risk scores. An example of an autoregressive model that can be used is as follows:

$$x(t)=\text{sum}(k=1{:}p)B{\times}(t-k)+B0+e(k).$$

In this autoregressive model of order p, a future risk score is based on a linear combination of previous risk scores combined with a small error term e(k), where k is an index that runs from 1 to p and where B and B0 denote coefficients. The coefficients may be determined based on a set of previous risk scores for a set of subjects.

Although an example forecasting technique has been provided, those skilled in the art will understand that any other forecasting technique can be used. These techniques can depend on whether an intervention is present or absent. For example, the technique may include two autoregressive models (i.e. one for a group of subjects where an intervention is present and another for a group of subjects where an intervention is absent), or a single autoregressive model where intervention is a co-variate.

In some embodiments, the likelihood of occurrence of a medical event for the subject is determined based on whether a medical event occurred for the subject of the selected at least one risk profile (such as in the predetermined time frame). For example, the determination may be based on whether an endpoint of a medical event is negative (i.e. unfavorable). Examples of unfavorable endpoints include but are not limited to morbidity, mortality, hospitalization, use of a medical service (such as emergency transport or an emergency department visit), or similar, or a combination thereof.

In this embodiment, it is identified whether a medical event occurred for the subject of the selected at least one risk profile and the likelihood of occurrence of a medical event for the subject is determined based on the identification. The likelihood of occurrence of the medical event for the subject may be determined as the percentage of the selected at least one risk profile for which a medical event occurred for the subject of the selected at least one risk profile. For example, if ten profiles are selected and two of those ten selected profiles are for subjects that had a medical event occur, the likelihood of occurrence of the medical event for the subject is determined to be two in ten (2/10) or 20%. Therefore, the more subjects of the selected at least one risk profile that had a medical event occur, the more likely it is determined that the medical event is to occur for the subject.

In some embodiments, it is identified whether a medical intervention occurred for the subject of the selected at least one risk profile and the likelihood of occurrence of a medical event for the subject is determined based on the identification. The likelihood of occurrence of the medical event for the subject may be determined as the percentage of the selected at least one risk profile for which a medical intervention occurred for the subject of the selected at least one risk profile. For example, if four profiles are selected and three of those four selected profiles are for subjects that had a medical intervention occur, the likelihood of occurrence of a medical event for the subject is determined to be three in four (3/4) or 75%. Therefore, the more subjects of the selected at least one risk profile that had a medical intervention occur, the more likely it is determined that a medical event is to occur for the subject if an intervention is not implemented or if a preventative action is not taken.

In some embodiments, it is identified whether a medical event occurred for the subject of the selected at least one risk profile and whether a medical intervention occurred for the subject. The likelihood of occurrence of a medical event for the subject is then determined based on this identification. For example, the likelihood of occurrence of a medical event for the subject may be determined as the percentage of the selected at least one risk profile for which one or both of a medical intervention and a medical event occurred for the subject of the selected at least one risk profile.

At block 212, a signal indicative of the determined likelihood of occurrence of the medical event for the subject is output. The control unit 102 of the apparatus 100 may be configured to output the signal. The signal may be output via a rendering component such as any one or more of a visual component (such as a user interface, a display screen, one or more lights, and/or any other visual component), a sound component (such as a speaker, a loud speaker, and/or any other sound component), a tactile feedback component (such as a vibration function and/or any other tactile feedback component) or any other rendering component. For example, the determined likelihood may be output as an alarm, a flag, a number, a percentage, a colored light (such as red, orange or green), or any other output or combination of outputs. In some embodiments, the signal may be output to a remote rendering component to be provided remotely (for example, via a phone line, the internet or any other communication means).

In some embodiments, it may be determined whether a medical intervention is to be implemented for the subject based on the determined likelihood of occurrence of the medical event and a signal indicative of the determination may be output. As above, the control unit 102 of the apparatus 100 may be configured to output the signal and the signal may be output via a rendering component such as any of those mentioned above or any other rendering component or combination of rendering components.

Based on the output signal from the rendering component, a user of the apparatus 100 (such as the subject themselves, a caregiver, a family member, a peer, or a healthcare professional) can decide whether an action such as an intervention needs to be taken and/or is justifiable to prevent occurrence of a medical event. In the case of determining that a medical event for the subject is likely (for example, if the likelihood of a medical event is determined to be above a threshold value), an action such as an intervention may take place to prevent the occurrence of the medical event. If no medical event occurred for any of the subjects of the selected at least one risk profile or the endpoint of the medical event is determined to be positive, it may be determined that occurrence of a medical event for the subject is unlikely. In this case, no action (e.g. intervention) takes place.

In some embodiments, the likelihood of occurrence of a medical event for the subject is determined based on a visual comparison of the subject risk profile and the selected at least one risk profile. The visual comparison can be used to decide whether an intervention is necessary to avoid (or lower the risk of) an occurrence of a medical event and may also be used to decide on the type of intervention to implement. The visual comparison may involve a comparison of the subject risk profile with a combination of risk profiles selected where an intervention occurred and risk profiles selected where no intervention occurred. Where it is determined that the risk scores of subjects without an intervention increased to a negative (i.e. unfavorable) endpoint whilst the risk scores of subjects with an intervention did not increase to a negative (i.e. unfavorable) endpoint, a user of the apparatus can decide that an intervention is necessary for the subject.

In an exemplary embodiment, a logistic regression model may be used that scores a likelihood of a hospitalization. For example, this may be a likelihood of hospitalization in the short term (such as within a week) and for a predetermined condition (such as heart failure). The logistic regression model may relate physiological characteristics (such as daily vital sign readings) and symptoms, which may be acquired through survey responses (e.g. shortness of breath, fatigue and swelling of ankles) to an outcome or event. In this exemplary embodiment, the physiological characteristics of body weight (BW), heart rate (HR) and blood pressure (BP) and the symptoms of shortness of breath (SoB), fatigue (F) and swelling of ankles (SoA) are related to an outcome Risk by means of a logistic function and a set of coefficients denoted by $\beta$, as follows:

$$\text{Risk}=\text{logistic}([1\ BW\ HR\ BP\ SoB\ F\ SoA]\beta)$$

After estimating the risk for the subject, the risk scores of other patients in the database are calculated using the same model. The risk scores of other patients may be pre-calculated and fetched from a memory unit to minimize computational load. By using a matching scheme, risk scores between subjects in the database and target subjects are compared and M closest matches are kept, where M is the number of allowed matches. A comparison technique such as those described earlier can be used to compute a match. Additionally, a length for an inspection window to apply on a selected risk profile of a subject selected from the database can be user definable. In other words, a user can define the quantity of data from the selected subject in the database to use for the matching scheme (for example, last week, last 5 days, one week in the preceding month, and so on). In this way, it is possible to focus on a particular phase of a timeline for a subject selected from the database.

In another exemplary embodiment, a database may contain an extensive follow-up history for subjects that comprises multiple risk scores over time, outcome of treatment options or even observed event occurrences. The follow-up history of the subject in the database is matched with a target subject. In this exemplary embodiment, a model scores the likelihood that the subject will experience heart failure in the year following hospital discharge. The model relates the demographical and clinical predictors of age, gender, BMI, Left ventricular ejection fraction (LVEF), N-terminal pro-brain natriuretic peptide(NT-proBNP) and hypertension, to an outcome Risk by means of a logistic function and a set of coefficients denoted by $\beta$, as follows:

$$\text{Risk}=\text{logistic}([1\ Age\ Gender\ BMI\ LVEF\ NT\text{-}proBNP\ Hypertension]\beta)$$

The result may allow a healthcare professional to make a clinical decision (for example, to decide on post-discharging services for the subject).

Figure 3:
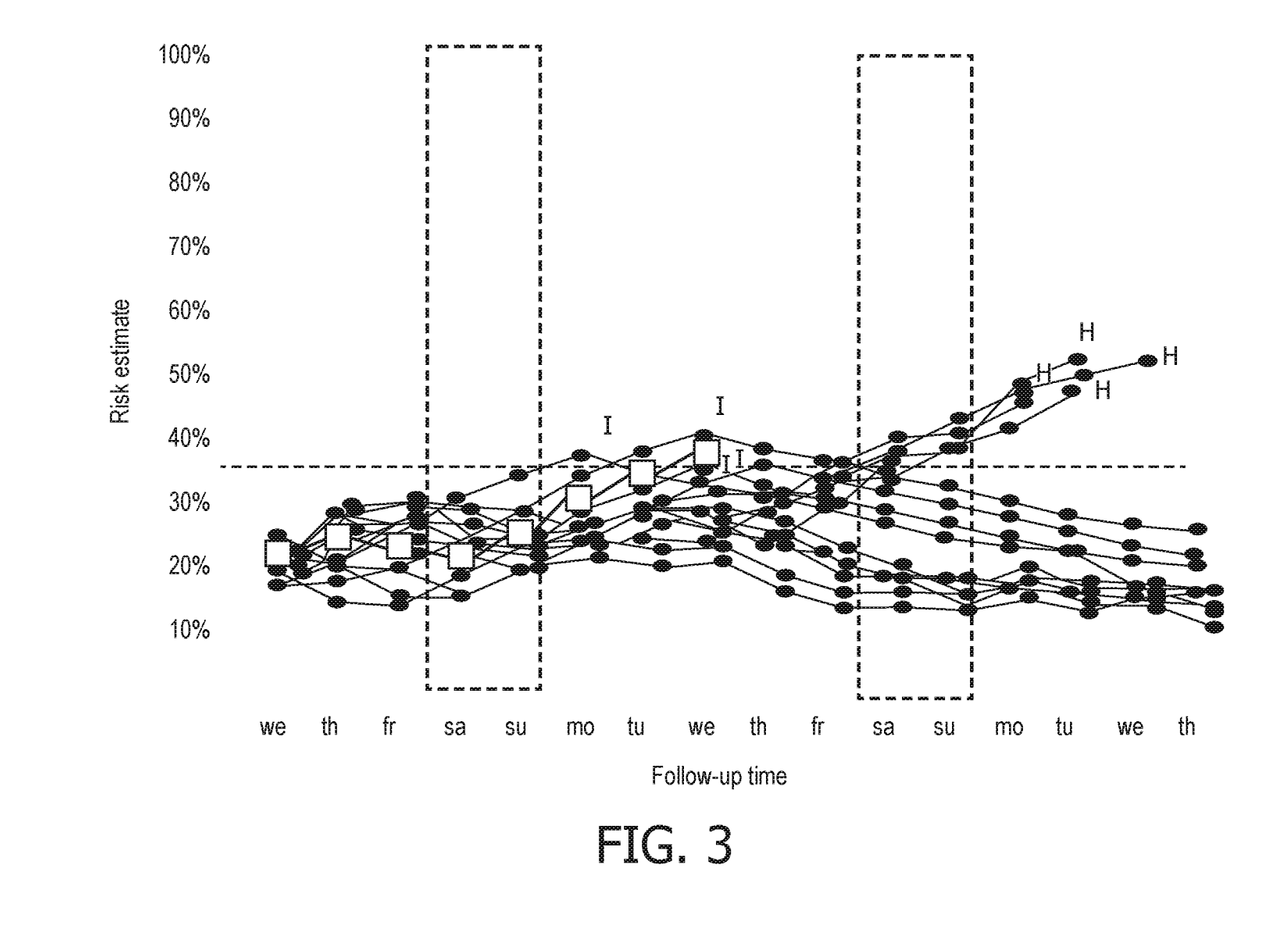
FIG. 3 is a graphical illustration of risk score estimates as a function of time according to an exemplary embodiment.

FIG. 3 is a graphical illustration of risk score estimates as a function of time according to an exemplary embodiment. In FIG. 3, more than two full weeks of daily risk scores of a target subject is aligned with a time series of risk scores from fifteen other subjects by matching risk scores. The dotted horizontal line represents a risk threshold (which is set at 35% in this exemplary embodiment) at which an intervention is recommended. In other words, an intervention is recommended when the likelihood of a medical event occurring is above 35%. Although the risk threshold is set at 35% in this exemplary embodiment, it will be understood that other risk thresholds may also be set. For example, the risk threshold may be set at 20%, 25%, 30%, 35%, 40%, 45%, or any intervening value. The risk scores of the subject (depicted in squares) are represented in absolute time, whereas the risk scores of the other subjects can be represented in relative time. The other subjects comprise a set of subjects in a stable condition (which can be seen to remain under the risk threshold), a set of subjects that received an intervention (denoted as I) and then stabilized, and a set of a subjects that experienced a hospitalization event (denoted as H). As illustrated in FIG. 3, the set of subjects that received an intervention while having a risk score above the 35% risk threshold showed improvement over time by a lowering of their risk score. In contrast, subjects that did not receive an intervention experienced a hospitalization event approximately seven days later following a further increase in their risk scores.

Figure 4:
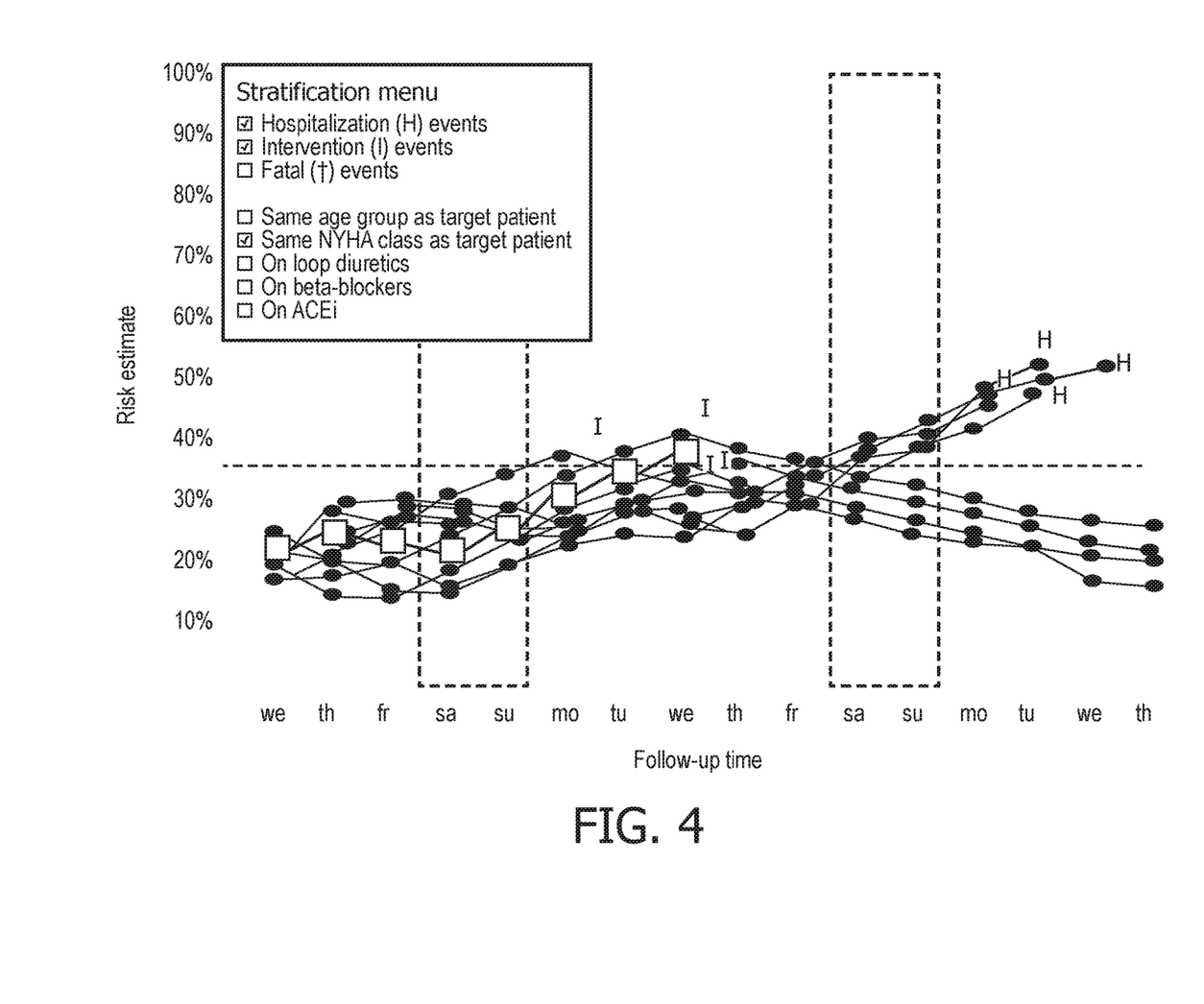
FIG. 4 is a graphical illustration of risk score estimates as a function of time according to another exemplary embodiment.

FIG. 4 is a graphical illustration of risk score estimates as a function of time according to another exemplary embodiment. In FIG. 4, more than a full week of daily risk scores of a target heart failure subject is aligned with a time series of risk scores from eight other subjects by matching risk scores and stratifying on hospitalization events, intervention events and the same New York Heart Association (NYHA) class for disease severity. The dotted horizontal line represents a risk threshold (which is set at 35%) at which an intervention is recommended. The graphical illustration may be rendered on a user interface device and can be interactive, allowing a user to scroll through the data. A stratified sub-set of subjects (instead of the entire database) can be intuitively selected by input of stratification criteria via the user interface device. For example, the stratification criteria can include display of only data for subjects in the same age group, suffering from the same disease severity, using identical medication, having experienced a hospitalization, intervention or a fatal event, or similar. In this way, a retrospective analysis can be performed to reveal potential differences between the risk score trajectories of a subject and the other subjects meeting the stratification criteria.

Figure 5:
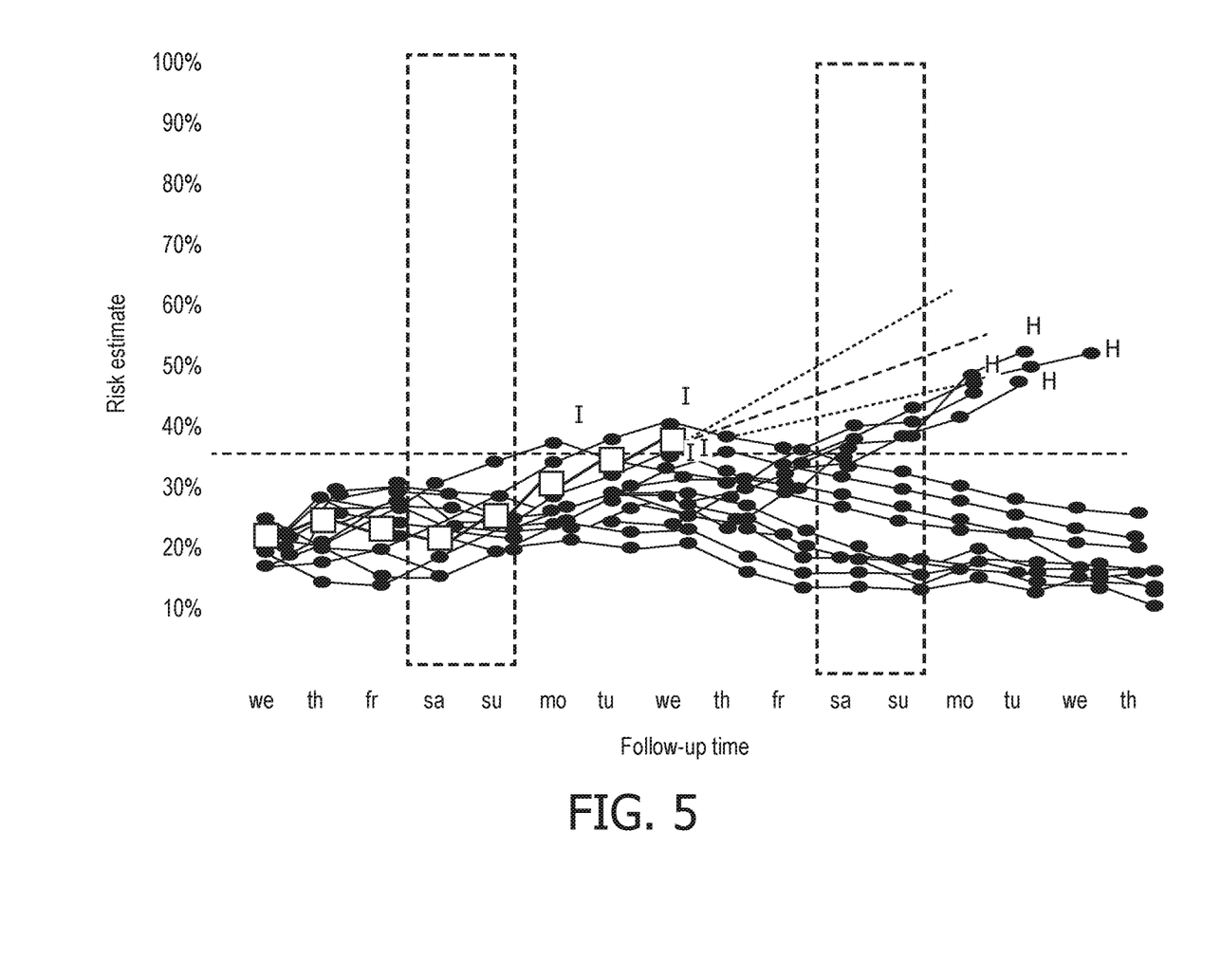
FIG. 5 is a graphical illustration of risk score estimates as a function of time according to another exemplary embodiment.

FIG. 5 is a graphical illustration of risk score estimates as a function of time according to another exemplary embodiment. In FIG. 5, more than one full week of daily risk scores of a target subject is aligned with a time series of risk scores from fifteen other subjects by matching risk scores. The most likely forecast of the time-series of risk scores for the target subject is displayed as a straight dotted line along with its confidence interval of 95%. This forecast estimates the risk scores with no intervention, which results in a hospitalization event (denoted by H), and the risk scores with an intervention (denoted by I), which prevents a hospitalization event.

There is therefore provided a method and apparatus for reliably and efficiently determining a likelihood of occurrence of a medical event for a subject. The method and apparatus can be useful in monitoring a subject at home (such as in a telehealth system, a personal emergency response system or other home monitoring system) and in a healthcare facility (such as a hospital, ambulance, or other healthcare facility).

A processor is one example of a controller which employs one or more microprocessors that may be programmed using software (e.g., microcode) to perform the required functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method for determining a likelihood of occurrence of a medical event for a subject, the method comprising:
   acquiring a subject risk profile for the subject based upon measurement, by a physiological characteristic sensor, of physiological characteristics of the subject, wherein the subject risk profile comprises a time series of risk scores for the subject;
   obtaining a plurality of other subject risk profiles for other subjects from a database, wherein the other subject risk profiles comprise a time series of risk scores for the other subjects;
   comparing the acquired subject risk profile to the obtained plurality of other subject risk profiles;
   selecting at least one risk profile from the obtained plurality of other subject risk profiles that most closely matches the acquired subject risk profile;
   determining the likelihood of occurrence of the medical event for the subject based on the selected at least one risk profile; and
   outputting a signal indicative of the determined likelihood of occurrence of the medical event for the subject.

2. The computer-implemented method according to claim 1, wherein the method further comprises:
   time-aligning the time series of risk scores in the obtained plurality of other subject risk profiles with the time series of risk scores in the acquired subject risk profile, wherein comparing the acquired subject risk profile to the obtained plurality of other subject risk profiles further comprises:
   comparing the time-aligned risk profiles.

3. The computer-implemented method according to claim 1, wherein the at least one risk profile from the obtained plurality of other subject risk profiles that most closely matches the acquired subject risk profile has identical or similar risk scores over time to the risk scores for the subject, and the similar risk scores are risk scores that differ by less than a predefined value from the risk scores for the subject.

4. The computer-implemented method according to claim 1, wherein the method further comprises:
   forecasting the time series of risk scores for the subject in a predetermined time frame based on the time series of risk scores in the selected at least one risk profile; and wherein determining the likelihood of occurrence of the medical event for the subject based on the selected at least one risk profile further comprises:
   determining the likelihood of occurrence of the medical event for the subject based on the forecasted time series of risk scores for the subject.

5. The computer-implemented method according to claim 1, wherein the subject risk profile comprises a plurality of risk scores for the subject and the obtained plurality of other subject risk profiles comprises respective risk scores for the other subjects.

6. The computer-implemented method according to claim 5, wherein selecting at least one risk profile from the obtained plurality of other subject risk profiles that most closely matches the acquired subject risk profile further comprises:
   selecting at least one risk profile from the obtained plurality of other subject risk profiles comprising risk scores that most closely match the respective risk scores of the subject risk profile.

7. The computer-implemented method according to claim 1, wherein comparing the acquired subject risk profile to the obtained plurality of other subject risk profiles comprises:
   dividing the acquired subject risk profile for the subject and the obtained plurality of other subject risk profiles into a plurality of segments; and
   comparing the segments of the acquired subject risk profile with corresponding segments of the obtained plurality of other subject risk profiles; and wherein selecting at least one risk profile from the obtained plurality of other subject risk profiles that most closely matches the acquired subject risk profile comprises:
   selecting at least one risk profile from the obtained plurality of other subject risk profiles that has a segment comprising risk scores that most closely match the risk scores of the corresponding segment of the acquired subject risk profile.

8. The computer-implemented method according to claim 1, wherein determining the likelihood of occurrence of the medical event for the subject based on the selected at least one risk profile comprises:
   identifying whether the medical event occurred for the subject of the selected at least one risk profile and/or identifying whether a medical intervention occurred for the subjects of the selected at least one risk profile; and
   determining the likelihood of occurrence of the medical event for the subject based on the identification.

9. The computer-implemented method according to claim 8, wherein determining the likelihood of occurrence of the medical event for the subject based on the identification comprises:
   determining the likelihood of occurrence of the medical event for the subject as the percentage of the selected at least one risk profile for which the medical event occurred for the subject of the selected at least one risk profile or for which the medical intervention occurred.

10. The computer-implemented method according to claim 1, further comprising:
    determining whether to instruct a medical intervention for the subject based on the determined likelihood of occurrence of the medical event; and
    outputting a signal indicative of the determination.

11. The computer-implemented method according to claim 1, wherein the risk scores are values determined based on any one or more of: one or more physiological characteristics of the subject; one or more symptoms of the subject; clinical information for the subject; and demographical information for the subject.

12. A non-transitory computer readable medium, the non-transitory computer readable medium having computer readable code embodied therein, the computer readable code being configured such that, on execution by a suitable computer or processor, the computer or processor is caused to perform
 instructions for acquiring a subject risk profile for the subject based upon measurement, by a physiological characteristic sensor, of physiological characteristics of the subject, wherein the subject risk profile comprises a time series of risk scores for the subject;
 instructions for obtaining a plurality of other subject risk profiles for other subjects from a database, wherein the other subject risk profiles comprise a time series of risk scores for the other subjects;
 instructions for comparing the acquired subject risk profile to the obtained plurality of other subject risk profiles;
 instructions for selecting at least one risk profile from the obtained plurality of other subject risk profiles that most closely matches the acquired subject risk profile;
 instructions for determining the likelihood of occurrence of the medical event for the subject based on the selected at least one risk profile; and
 instructions for outputting a signal indicative of the determined likelihood of occurrence of the medical event for the subject.

13. An apparatus for determining a likelihood of occurrence of a medical event for a subject, the apparatus comprising a control unit configured to:
 acquire a subject risk profile for the subject based upon measurement, by a physiological characteristic sensor, of physiological characteristics of the subject, wherein the subject risk profile comprises a time series of risk scores for the subject;
 obtain a plurality of other subject risk profiles for other subjects from a database, wherein the other subject risk profiles comprise a time series of risk scores for the other subjects;
 compare the acquired subject risk profile to the obtained plurality of other subject risk profiles;
 select at least one risk profile from the obtained plurality of other subject risk profiles that most closely matches the acquired subject risk profile; and
 determine the likelihood of occurrence of the medical event for the subject based on the selected at least one risk profile; wherein the apparatus further comprises an output unit operatively connected to the control unit configured to
 output a signal indicative of the determined likelihood of occurrence of the medical event for the subject.

14. The apparatus as claimed in claim 13, wherein the subject risk profile is based on one or more physiological characteristics of the subject, one or more symptoms of the subject, clinical information for the subject, and/or demographic information for the subject, and wherein the control unit is configured to
 acquire the one or more physiological characteristics of the subject by controlling a physiological characteristic sensor to measure the one or more physiological characteristics of the subject, and to
 acquire the one or more symptoms of the subject, the clinical information of the subject, and/or the demographic information for the subject from a user interface device.

15. The apparatus as claimed in claim 13, wherein the apparatus is part of a general purpose computing device.

\* \* \* \* \*